United States Patent [19]

Kishimoto et al.

[11] Patent Number: 5,252,724
[45] Date of Patent: Oct. 12, 1993

[54] METHOD OF EXTRACTING PARTICULAR NUCLEIC ACID FRAGMENT

[75] Inventors: Toshihiko Kishimoto; Shin-Ichiro Niwa; Atsushi Uno, all of Osaka, Japan

[73] Assignee: Sumitomo Electric Industries, Ltd., Osaka, Japan

[21] Appl. No.: 700,694

[22] Filed: May 16, 1991

[30] Foreign Application Priority Data

May 17, 1990 [JP] Japan ................................. 2-127702

[51] Int. Cl.$^5$ ............................................. C12N 15/10
[52] U.S. Cl. ...................................... 536/25.4; 435/6; 435/91.52; 435/91.53; 935/19
[58] Field of Search ...................... 435/6, 91; 536/25.4

[56] References Cited

FOREIGN PATENT DOCUMENTS 0224126  6/1987  European Pat. Off. .
0356021  2/1990  European Pat. Off. .
8912695 12/1989  PCT Int'l Appl. .

OTHER PUBLICATIONS

Wolf et al. (1987), Nucl. Acids Res. 15(7):2911–2926.
Carrano et al. (1989), Genomics 4:129–136.
Ray Wu et al, "Adaptors, Linkers and Methylation", Methods in Enzymology, vol. 152, 1987, pp. 343–349.

*Primary Examiner*—Richard A. Schwartz
*Assistant Examiner*—Philip W. Carter
*Attorney, Agent, or Firm*—Cushman Darby & Cushman

[57] ABSTRACT

A method of extracting a particular nucleic acid fragment containing a nucleic acid sequence of interest from a nucleic acid or nucleic acids mixture, comprising the steps of:
(1) digesting the nucleic acid or nucleic acids mixture with restriction enzymes to obtain a mixture of nucleic acid fragments, said restriction enzymes consisting of (A) two different enzymes capable of producing the particular nucleic acid fragment bearing predetermined and distinct restriction ends on its 5' and 3' terminals and (B) one or more restriction enzymes different from (A), for which the particular nucleic acid fragment contains no relevant restriction sites;
(2) preparing two distinct DNA linkers capable of binding to the respective restriction ends of the particular nucleic acid fragment;
(3) allowing the linkers to react with the mixture of nucleic acid fragments;
(4) subjecting the resulting reaction mixture to the first hybridization with an immobilized probe complementary to one of the linkers;
(5) isolating the hybridized nucleic acid fragment from the probe;
(6) subjecting the isolated nucleic acid fragment to the second hybridization with an immobilized probe complementary to the other linker; and
(7) isolating the hybridized nucleic acid fragment from the probe.

11 Claims, 1 Drawing Sheet

METHOD OF EXTRACTING PARTICULAR NUCLEIC ACID FRAGMENT

The present invention relates to a method of extracting a particular nucleic acid fragment from a nucleic acid or nucleic acids mixture.

Nowadays, with the progress of genetic engineering, there have been increasing a necessity of extracting or separating a particular nucleic acid fragment from a nucleic acid or nucleic acids mixture in various fields including medicine and agriculture. A method of extracting a particular nucleic acid fragment containing a known base sequence from a nucleic acid or nucleic acids mixture is already known (Cell Engineering, vol. 8, No. 7, 1989). According to the known method, two or three distinct probes, each consisting of 20 to 30 bases, are prepared on the basis of the base sequence of a nucleic acid fragment of interest. These probes are then attached at their terminal to a carrier such as a gel or a membrane through a covalent bond, thereby forming immobilized probes. On the other hand, a nucleic acid containing the desired nucleic acid fragment is collected together with other nucleic acids from cells, followed by heat denaturation. The heat-denatured nucleic acids are mixed with the immobilized probes for hybridization, after which the immobilized probes thus hybridized are recovered by centrifugation. The immobilized probes thus recovered are heat-treated, after which the nucleic acid containing the desired nucleic acid fragment is recovered by means of electrophoresis.

The aforementioned method has the following drawbacks:

1. The immobilized probes may have a possibility of hybridizing with undesired fragments, because they are prepared by utilizing part of the sequence of the desired nucleic acid fragment. Accordingly, selection efficiency is low. In addition, this method lacks simplicity and applicability, because it is limited to the extraction of nucleic acids having a known sequence.

2. The hybridization of the collected DNAs with the immobilized probes is conducted only once with the use of only one target sequence, i.e., complementary sequence, and therefore, accuracy is low.

3. The recovery of a nucleic acid fragment by electrophoresis requires a complicated operation and much time.

The present inventors have devoted themselves to a study for overcoming the drawbacks of the conventional method as mentioned above, and accomplished the present invention on the basis of the findings that a nucleic acid fragment containing the desired nucleic acid sequence can be extracted with high efficiency by digesting a nucleic acid or nucleic acids mixture with restriction enzymes selected so as to digest the nucleic acid or acids in the manner that a desired nucleic acid fragment bearing desired distinct restriction ends on 5' and 3' terminals is obtained, ligating two distinct DNA linkers to each of these restriction ends, and performing two times hybridization by using the immobilized probes complementary to the respective linkers.

Thus, the present invention provides a method of extracting a particular nucleic acid fragment containing a nucleic acid sequence of interest from a nucleic acid or nucleic acids mixture, comprising the steps of:

(1) digesting the nucleic acid or nucleic acids mixture with restriction enzymes to obtain a mixture of nucleic acid fragments, said restriction enzymes consisting of (A) two different enzymes capable of producing the particular nucleic acid fragment bearing predetermined and distinct restriction ends on its 5' and 3' terminals and (B) one or more restriction enzymes different from (A), for which the particular nucleic acid fragment contains no relevant restriction sites;

(2) preparing two distinct DNA linkers capable of binding to the respective restriction ends of the particular nucleic acid fragment;

(3) allowing the linkers to react with the mixture of nucleic acid fragments;

(4) subjecting the resulting reaction mixture to the first hybridization with an immobilized probe complementary to one of the linkers;

(5) isolating the hybridized nucleic acid fragment from the probe;

(6) subjecting the isolated nucleic acid fragment to the second hybridization with an immobilized probe complementary to the other linker; and (7) isolating the hybridized nucleic acid fragment from the probe.

Figure 1:
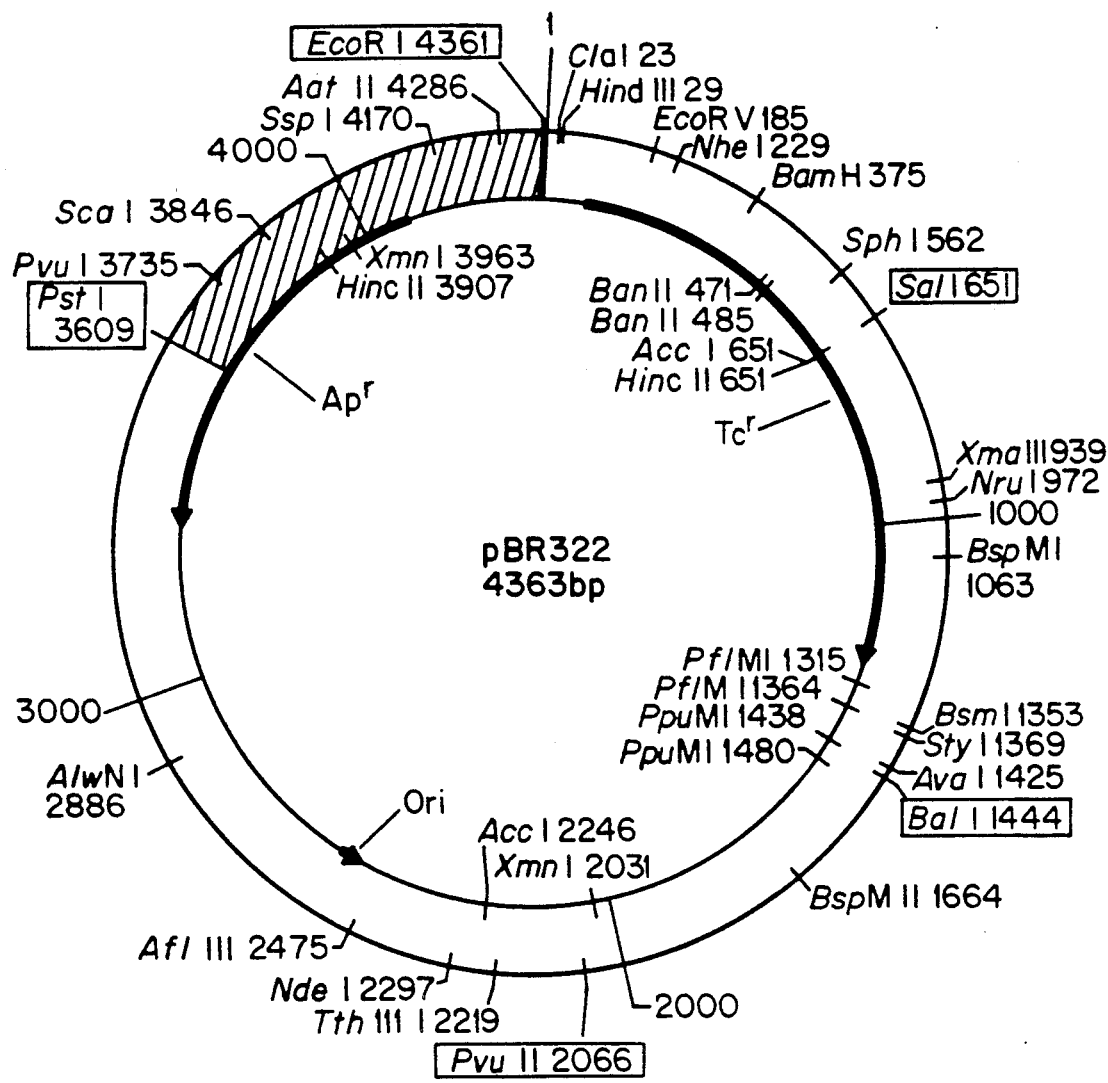
FIG. 1. Restriction map of pBR322.

The present invention will be described below in more detail.

The term "a nucleic acid or nucleic acids mixture" refers to a single DNA or a DNAs mixture collected from cells. The term "nucleic acid" primarily means both DNA and RNA, although it is sometimes used to denote DNA where there is no possibility of misunderstanding from the context.

The term "a particular nucleic acid fragment containing a nucleic acid sequence of interest" or "a desired nucleic acid fragment" refers to a fragment or fragments consisting of the desired nucleic acid sequence, and also a fragment or fragments which contain additional sequences derived from linkers or the like, as well as the desired nucleic acid sequence, said additional sequences causing no adverse affect to the desired nucleic acid sequence.

The term "restriction end(s)" means 5' and/or 3' end of a given nucleic acid fragment which has been formed through digestion of the nucleic acid by restriction enzyme(s).

The term "extract" or "extracting" in this specification means separation and isolation of a desired nucleic acid fragment from a nucleic acid or nucleic acids mixture, or concentration of the desired nucleic acid fragment from a mixture of various nucleic acid fragments obtained by digestion of the nucleic acid or acids with restriction enzymes.

The novel method of extracting a nucleic acid fragment according to the present invention comprises the following steps:

i) A nucleic acid fragment to be extracted is determined.

ii) One or more of nucleic acids, in which the desired nucleic acid fragment moiety is contained, are treated with restriction enzymes selected for obtaining the nucleic acid fragment of interest, wherein the selection of the restriction enzymes is conducted as follows: (1) two different restriction enzymes are selected so that they give different restriction ends at the 5' terminal and 3' terminal of the desired nucleic acid fragment; and (2) other one or more restriction enzymes, for which the desired nucleic acid fragment contains no restriction site(s), are added in order to decrease the possibility that undesired fragments may have the same restriction ends as those of the desired fragment.

iii) Two different linkers capable of binding specifically to the restriction ends of the desired nucleic acid fragment are added to the nucleic acid fragments obtained above.

iv) Each of the linkers is allowed to ligate to the corresponding restriction end by addition DNA ligase.

v) A probe complementary to each of the two linkers is immobilized on a carrier to form an immobilized probe.

vi) The solution obtained in step iv) is subjected to denaturation treatment.

vii) The immobilized probe complementary to one of the linkers, which has been prepared in step v), is added to the solution in step vi) and allowed to stand for performing hybridization.

viii) The immobilized probe phase is recovered and subjected to denaturation, and the hybridized nucleic acid fragments are then recovered.

ix) The nucleic acid fragments obtained in step viii) are used to repeat the aforementioned steps vi), vii), and viii) using the other immobilized probe complementary to the other linker prepared in step v).

The linkers used in the above method of the present invention may be a single- or double-stranded nucleic acid linker which has at its end a specific base sequence capable of annealing with either of two restriction ends formed by the action of the selected restriction enzymes. Such linkers include naturally-occurring single- or double-stranded DNA or RNA which may have been appropriately excised or denatured. Such linkers can also be synthesized by any one of the methods which are well known to those skilled in the art. For example, they may be synthesized using a DNA synthesizer manufactured by Applied Biosystems Inc., in accordance with the accompanying instructions. Where the restriction enzymes selected for providing unique restriction ends at 5' and 3' terminals of the desired nucleic acid fragment are Eco RI and Pst I, the linkers to be used may be those having the following base sequences:

Eco RI linker

5' GCAACCATGCCTAAGTTTG 3' (SEQ ID NO:1)
3' CGTTGGTACGGATTCAAACTTAA 5' (SEQ ID NO:2)

Pst I linker

5' TTCCGTATGGCATGCCTCCCTGCA 3' (SEQ ID NO:3)
3' AAGGCATACCGTACGGAGGG 5' (SEQ ID NO:4)

The probes used in the method of the present invention may be nucleic acid fragments at least partially complementary to the linkers having a predetermined base sequence. Such nucleic acid fragments include naturally-occurring single- or double-stranded DNA or RNA which may have been appropriately excised or denatured, and artificially-synthesized DNA or RNA. For instance, the probes can be obtained by synthesizing a DNA molecule complementary to all or part of the linker DNA sequence. The DNA fragments used as the probes may be a single- or double-stranded molecule. When double-stranded DNA is used as a probe, it may be denatured after immobilization. The probe contains at 5' terminal a DNA sequence which is convenient for allowing the probe to bind to a carrier. For instance, Amino-Link II (available from Applied Biosystems Inc.) described in Example below is a typical example for the sequence.

The carrier used for preparing immobilized probes is selected from the group consisting of particles and membranes. Specific examples of the membranes are naturally-occurring or synthetic organic polymer membranes (e.g., nylon membrane, nitrocellulose membrane polytetrafluoroethylene membrane, polyethylene membrane, etc). Other examples include inorganic polymer membranes (e.g., graphite, polous glass, silica, etc), metal membranes (e.g., aluminium, apatite, etc), ceramic membranes (e.g., alumina, silicon nitride, etc), and NaCl crystals, all of which may be chemically or physically modified on the surface.

Specific examples of the particles are organic polymer particles (e.g., nylon, nitrocellulose, cellulose, polytetrafluoroethylene, polyethylene, etc), inorganic polymer particles (e.g., graphite, polous glass, silica, etc), metal particles (e.g., aluminium, apatite, etc), and ceramic particles (e.g., alumina). These particles may be employed after tightly dispersed on a surface of an appropriate object.

The above-mentioned organic polymers may be used after oxidation, reduction, or hydrolysis, or physical treatment such as plasma irradiation. The surface of the inorganic polymer particles, metal particles and ceramic particles may be chemically or physically modified before use by, for example, ion-plating.

Further, the carriers may be gel such as agarose gel, polyacrylamide gel, and those in dried form or in high viscous state.

Preferred particle size of the above-mentioned particles may be 0.1 $\mu$m -500 $\mu$m, most preferably 1 $\mu$m -100 $\mu$m, in order to secure easier dispersion in a sample solution and easier recovery by centrifugation. However, the above size dimensions are not critical as far as the particles employed do not adversely affect the reaction between the immobilized probe and the sample, and the recovery of the immobilized probe.

A method of binding a probe to a carrier is well known and conducted under known conditions. Thus, the binding method may be selected from those listed below depending on the mode of chemical modifications on particular probe and carrier employed.

1. The hydroxy group, preferably diol group, on the nucleic acid probe or the carrier is activated, and the activated hydroxy group is reacted with the amino group on the carrier or the probe. The agents used for the activation of the hydroxy group includes trifluoroethane-sulfonylchloride (hereinafter referred to as tresyl chloride) (K. Nillson and K. Mosbach, Biochem. Biophys. Res. Commun., 102, 449, 1981), CNBr (R. Axen et al., Nature, 214 1302, 1967), trichlorotriazine (T. H. Finlay et al., Anal. Biochem., 87 77, 1978), epichlorohydrin (I. Matsumoto et al., J. Biochem., 85 1091, 1979), bisoxirane (L. Sundberg and J. Porath, J. Chromatogr., 90 87, 1974), divinylsulfonic acid (J. Porath, Meth. Enzymol., 34 27, 1974), benzoquinone (J. Brandt et al., Biochem. Biophys. Acta., 386 196, 1975), and carbonyldiimidazole (G. S. Bethell et al., J. Biol. Chem., 254 2572, 1979).

2. The carboxy group on the nucleic acid probe or the carrier is activated, and the activated carboxy group is reacted with the amino group on the carrier or the probe. The agents used for the activation of the carboxy group includes carbodiimides such as water-soluble carbodiimide (A. Tengblad, Biochem. J., 199 297, 1981;

M. Funabashi et al., Anal. Biochem., 126 414, 1982) and 2-ethoxy-1-ethoxycarbonyl-1,2-dihydroquinoline (EEDQ) (G. Saccomani et al., J. Biochem., 256 12405, 1981; B. Bellenau and G. Malek, J. Am. Chem. Soc., 90 1651, 1968).

3. The desired DNA probe is linked, by the use of DNA ligase, to a nucleic acid which has been already been bound to a carrier by a conventional method non-specifically.

4. The probe is bound to the carrier by the reaction between the hydrazide group and the aldehyde group or the hydrazide group and the carboxy group thereon. The reaction between the hydrazide group and the aldehyde group yields a hydrazone group, which is subsequently reduced to form a covalent bond (Jonathan N. Kremsky et al., Nucleic Acid Research 1987, Vol. 15, p.2891 ). The reaction between the hydrazide group and the carboxy group may be conducted in the presence of carbodiimides described above.

5. The probe is bound to the carrier by introducing a certain group (for instance, biotin) into either of them, and another group (for instance, avidin) having affinity thereto into the other, and subsequently allowing to react these groups (Jonathan N. Kremsky et al., supra).

6. The thiol groups on both probe and carrier are activated and allowed to react each other (K. Bocklehurst et al., Biochem. J., 133 573, 1973).

7. The amino groups on both probe and carrier are allowed to react by bromoacetamide method (P. Cuatrecasas, J. Biol. Chem., 245 3059, 1970).

8. The probe is linked to the carrier via non-specific absorption or electrostatic absorption.

More detailed procedure for binding a probe to a carrier is provided below.

Use of single-stranded DNA

When a DNA probe contains one or more extra nucleotide molecules at the terminal, or when it contains chemically-modified nucleotide molecule(s) at the terminal, the extra nucleotide molecule(s) or modified nucleotide molecule(s) can be used for the binding to a carrier. For this purpose, the following procedure may be used.

1) A single-stranded DNA carrying a functional group suitable for immobilization, such as —NH$_2$ or —COOH, at the terminal is prepared in the following manner. Where the DNA is artificially synthesized, commercially available DNA synthesizer (for instance, ABI Corp., Type 391, PCR-MATE) may be used. Introduction of the functional group may be conducted according to one of the following methods.

i) Hexylamino group can be introduced into the terminal molecule of the DNA probe by the use of a DNA synthesizer according to the following reaction scheme (see User Bulletin, No. 49, August 1988, issued by ABI Corp.).

Single-Stranded DNA-Carboxy Terminal-OH
+

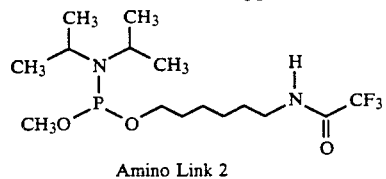

Amino Link 2

↓

Single-Stranded DNA 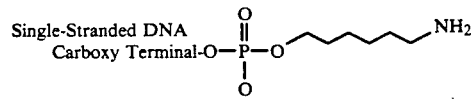
Carboxy Terminalii) The following linker can be introduced into the terminal of a DNA probe using a DNA synthesizer (for instance, ABI Corp., Type A-391 EP PCR-MATE), and the terminal of the linker can be converted to an aldehyde or carboxy group.

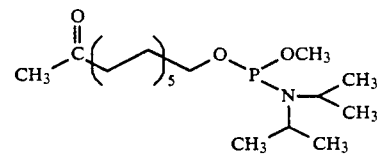

The aldehyde group formed at the terminal of the linker can be reacted with a hydrazide compound of biotin to produce a biotin which is capable of specifically reacting with an avidin to form a complex (Jonathan N. Kremsky et al., supra).

iii) One to some tens nucleotides having an amino group can be attached to the terminal of the DNA probe using a DNA synthesizer.

iv) A base suitable for the linkage with a carrier or its reactive derivative can be introduced into the terminal of the DNA probe using terminal transferase (Deug G. and WuR., Methods in Enzymology, Vol.100, p.96-116, 1983).

2) A single-stranded DNA complementary to the single-stranded DNA probe moiety in the above Step 1 is prepared using the same DNA synthesizer as in the Step 1, and the two DNAs are annealed to form a double-stranded DNA.

3) A carrier is bound to the double-stranded DNA to prepare an immobilized double-stranded DNA probe.

4) The immobilized double-stranded probe is denatured by heat (about 40° C. or above) or an alkali addition in an aqueous salt solution, such as 2.4M tetraethylammonium chloride aqueous solution, appropriately diluted 10 x SSC (1.5M NaCl and 0.15M sodium citrate; pH 7.0), or 0.1-2M NaCl aqueous solution. The mixture is centrifuged, and an immobilized single-stranded DNA is recovered as the solid phase.

Use of double-stranded DNA

When a double-stranded DNA contains one or more of extra nucleotide molecules at the terminal of one of the strands, the DNA can be linked, at its terminal, to a carrier with or without chemical modification of the extra nucleotide molecules. The resultant immobilized double-stranded DNA probe can be subjected to the above-mentioned Step 4) to obtain an immobilized single-stranded DNA probe.

The above-noted double-stranded DNA containing extra nucleotide molecules at the terminal of one of the strands may be prepared using one of the methods listed below.

i) A base suitable for the linkage with a carrier or its reactive derivative can be introduced into the terminal of only one of the two strands by the use of terminal transferase.

ii) A double-stranded DNA can be digested with a restriction enzyme so that a single-stranded moiety may be formed at the terminal.

iii) A DNA molecule having a functional group can be linked to a double-stranded DNA using DNA ligase. For instance, a double-stranded DNA is digested with two distinct restriction enzymes so that the DNA may have distinct restriction ends at the terminals. To the digested DNA is added a DNA which carries a functional group and which is capable of specifically binding to one of the above-noted restriction ends. Addition of DNA ligase to the resultant mixture yields a desired double-stranded DNA having a functional group at the terminal.

In the above process, 5' terminal of one of the strands, which is to be subsequently removed, may be dephosphorylated. Thus, a long double-stranded DNA, one of the terminals of which has an elongated single-strand, is prepared, and then the 5' terminal is dephosphorylated by the action of a dephosphorylation enzyme. The resultant DNA is then digested to obtain a desired DNA fragment having dephosphorylated 5' terminal.

iv) A double-stranded DNA is activated at 3' terminal by introducing trichlorotriazine into the —OH group at 3' terminal. When the —OH group at 5' terminal is desired to be activated, dephosphorylation treatment mentioned in the above item iii) is first conducted, followed by the reaction with trichlorotriazine. Since the —OH group at 5' terminal is more reactive than that at 3' terminal, the former can be preferentially and exclusively activated.

After the desired nucleic acid fragment bound to the DNA linker has been hybridized with the immobilized probe, the immobilized probe can be recovered by conventional methods such as 1) centrifugation, 2) filtration, 3) sedimentation, and 4) removal of supernatant fluid.

Denaturation which is performed to separate the desired nucleic acid fragment from the immobilized probe can be attained by 1) heat denaturation (usually at a temperature of 60° C. to 95° C.), 2) alkali denaturation (usually, by the addition of NaOH to a final concentration of about one normality (1N)), and 3) denaturation by the addition of formaldehyde, urea, or the like. An appropriate combination thereof can also be used.

As described above, the essence of the method of the present invention exists in that the desired nucleic acid fragment containing the desired sequence has at both terminals particular restriction ends which differ from each other, and that the desired nucleic acid fragment is subjected to hybridization two times by using two different probes, each of which is complementary to either of the linkers bound to the restriction ends of the fragment.

Thus, according to the method of the present invention, hibridization efficiency is very high, because probes complementary to the preselected linkers are used. In addition, the desired nucleic acid fragment can be obtained with high purity, because two hybridizations are performed using a different probe each time, said probe being complementary to either of two different linkers bound to the desired fragment. As a result, extraction can be conducted with high efficiency by a simple operation. Moreover, because the extraction is based on the hybridization of linkers with probes, the method is independent of the base sequence of the nucleic acid fragment of interest, and it is also easy to establish the reaction conditions. This indicates that it may be possible to extract a DNA fragment of which base sequence is not known by the method of the present invention.

Furthermore, according to the method of the present invention, it is possible to recover a nucleic acid fragment without using a complicated and time-consuming means such as electrophoresis.

The following detailed examples are presented by way of illustration of certain specific embodiments of the invention.

In the accompanying drawing, FIG. 1 shows a complete restriction map of plasmid pBR322.

EXAMPLE 1

Extraction of Eco RI-Pst I fragment from plasmid pBR322

This example illustrates an extraction of the desired nucleic acid fragment (hereinafter referred to as Fragment A) according to the method of the present invention, said Fragment A being part of the plasmid pBR322 derived from E. coli.

1) Determination of restriction sites at both ends of Fragment A and digestion of pBR322

The restriction map of pBR322 is well known in the art and shown in the accompanying drawing of FIG. 1. In this figure, the hatched area indicates the desired Fragment A. The restriction enzymes used for the digestion of pBR322 are shown by the box. It can be seen from the restriction map that the both ends of Fragment A can be digested with restriction enzymes Pst I and Eco RI and that there are no Sal I, Bal I, and Pvu II sites in Fragment A. Therefore, the treatment of pBR322 with the noted five restriction enzymes cannot produce any fragments other than Fragment A, which have at their both ends Pst I- and Eco RI-restriction ends.

Thus, pBR322 was treated with Eco RI, Sal I, Pst I, Pvu II, and Bal I in the manner as described below and obtained a mixture of nuclcic acid fragments containing Fragment A. The restriction enzymes used are all available from Takara Shuzo Co. Detailed procedure is described below.

First, the reaction mixture 1 having the following composition is allowed to react at 37° C. for 1 hour, followed by heat-treatment at 60° C. for 5 minutes to terminate the reaction. Phenol extraction is conducted, and the extract is then subjected to ethanol precipitation, followed by drying.

| Reaction mixture 1: | |
|---|---|
| Composition | Content |
| pBR322 | 2 μl (0.5 μg/μl) |
| Eco RI | 2 μl (5 U/μl) |
| Pst I | 2 μl (5 U/μl) |
| Sal I | 2 μl (5 U/μl) |
| High salt concentration buffer (Takara Shuzo) | 3 μl (×10 conc.) |
| H₂O | 19 μl |
| Total | 30 μl |

Next, for the purpose of further digestion with restriction enzyme Pvu II, the dried DNA obtained above is dissolved in 16 μl of water, and allowed to react at 37° C. for 1 hour in the reaction mixture 2 having the following composition, followed by heat-treatment at 60° C. for 5 minutes to terminate the reaction. Phenol extraction is conducted, and the extract is then subjected to ethanol precipitation, followed by drying.

| Reaction mixture 2: | |
|---|---|
| Composition | Content |
| DNA solution | 16 μl |
| Medium salt concentration buffer (Takara Shuzo) | 2 μl (×10 conc.) |
| Pvu II | 2 μl (5 U/μl) |
| Total | 20 μl |

For the purpose of further digestion with Bal I, the dried DNA obtained above is dissolved in 35 μl of water, and allowed to react at 37° C. for 1 hour in the reaction mixture 3 having the following composition, followed by heat-treatment at 60° C. for 5 minutes to terminate the reaction. Phenol extraction is conducted, and the extract is then subjected to ethanol precipitation, followed by drying.

| Reaction mixture 3: | |
|---|---|
| Composition | Content |
| DNA solution | 35 μl |
| Bal I buffer (Takara Shuzo) | 5 μl (×10 conc.) |
| Bal I | 10 μl |
| Total | 50 μl |

2) Preparation of DNA linkers

2a) Preparation of Eco RI linker

An Eco RI linker having the following sequence is synthesized.

Eco RI linker

5' GCAACCATGCCTAAGTTTG 3' (SEQ ID NO: 1)

3' CGTTGGTACGGATTCAAACTTAA 5' (SEQ ID NO: 2)

The above two single-stranded DNA molecules complementary to each other are synthesized using a DNA synthesizer (391 PCR-MATE model EP) available from Applied Biosystems Inc., in accordance with the description of the accompanying manual. Then, the synthesized DNA molecules are purified by a cutting purification method described in the manual.

The purified single-stranded DNA molecules (each 1 μg/μl in water, 5 μl) are mixed together and allowed to stand at 30° C. for 1 hour to allow annealing, thereby yielding a double-stranded DNA molecule. Then, the 5' end of the resulting double-stranded DNA molecule is phosphorylated. The phosphorylation is conducted at 37° C. for 1 hour in the following reaction mixture 4, and then the reaction is terminated by heat-treatment at 65° C. for 5 minutes.

| Reaction mixture 4: | |
|---|---|
| Composition | Content |
| Double-stranded DNA (1 μg/μl) | 2 μl |
| T4 polynucleotide kinase (10 U/μl) | 4 μl |
| ×10 T4 kinase buffer | 2 μl |
| 10 mM ATP | 2 μl |

| Reaction mixture 4: | |
|---|---|
| Composition | Content |
| (gamma-$^{32}$p) ATP (2 μM, 50 μCi) | 5 μl |
| H$_2$O | 5 μl |
| Total | 20 μl (0.1 μg DNA/μl) |

2b) Preparation of Pst I linker

A Pst I linker having the following sequence is synthesized.

Pst I linker

5' TTCCGTATGGCATGCCTCCCTGCA 3' (SEQ ID NO: 3)

3' AAGGCATACCGTACGGAGGG 5' (SEQ ID NO: 4)

The DNA synthesis, purification, and annealing of the single-stranded DNA molecules, and phosphorylation are conducted in the same way as described in Step 2a).

3) Binding of linkers to Fragment A

The linkers prepared in Step 2) are mixed with the pBR322 digestion products prepared in Step 1) so that the linkers may ligate to the desired DNA fragment. A Takara DNA ligation kit (manufactured by Takara Shuzo Co.) is used for this purpose. Thus, the DNA fragments mixture is dissolved in 20 μl of TE buffer (10 mM Tris-HCl, pH 8.0, and 1 mM EDTA) and allowed to react overnight at 16° C in the following reaction mixture 5, after which it is subjected to ethanol precipitation and evaporated to dryness.

| Reaction mixture 5: | |
|---|---|
| Composition | Content |
| DNA fragments mixture | 20 μl |
| Eco RI linker | 5 μl (0.1 μg/μl) |
| Pst I linker | 5 μl (0.1 μg/μl) |
| Solution A | 240 μl |
| Solution B | 30 μl |

Note)
The solutions A and B are reaction mixtures contained in the Takara DNA ligation kit.

4) Preparation of immobilized probes

Four DNA probes having the base sequences shown below were synthesized using a DNA synthesizer (391 PCR-MATE model EP) of Applied Biosystems Inc., in accordance with the description of the accompanying manual. To the 5' end of each probe, there was attached Amino-Link II (i.e., DNA linker) for binding to a carrier.

Amino-Link II is commercially available from ABI Corp. and is described in Applied Biosystem Inc. User Bulletin No. 49, August 1988, which is represented by the following formula.

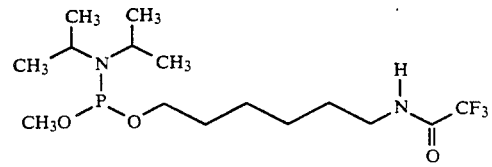

Probe 1: H$_2$N-(Amino-Link II]-GCAACCATGC-CTAAGTTTG (SEQ ID NO: 1)

Probe 2: CGTTGGTACGGATTCAAACTTAA (SEQ ID NO: 2)-(Amino-Link II)-NH$_2$
Probe 3: H$_2$N-(Amino-Link II)-TTCCGTATG-GCATGCCTCCCTGCA (SEQ ID NO: 3)
Probe 4: AAGGCATACCGTACGGAGGG (SEQ ID NO: 4)-(Amino-Lin II)-NH$_2$ The probes 1 and 2 are complementary to the Eco RI linker, and the probes 3 and 4 to the Pst I linker. These probes 1 to 4 are independently immobilized on a separate gel. Immobilization is performed as follows:

(1) Activation of gel

Trifluoroethanesulfonyl chloride (Tresyl chloride) (K & K or Fluka), which is used in the following procedure, tends to be decomposed by water at a pH higher than or equal to 3, and therefore, the following operation is performed using a dry box, a sterilized package filled with dry nitrogen gas, or the like, for the purpose of preventing moisture from invading. Acetone and pyridine to be used are dehydrated with a moleclar sieve for three or more days before use.

A 10 ml round bottom flask equipped with a stopper is charged with 1.5 ml of dehydrated acetone, 100 μl of pyridine, and a magnetic stirrer.

On the other hand, 1 g of gel (Shimpack diol 300 (Shimazu)) is quickly washed with 50 ml of dehydrated acetone on a #5 glass filter under suction, and immediately put into the aforementioned round bottom flask. Then, the flask is cooled in an ice bath (about 0° C.), and trecyl chloride (200 μl per gram of gel) is added dropwise over an approximately 1 minute with dry nitrogen gas being introduced into the flask under vigorous agitation.

After completion of the addition, the round bottom flask is closed with a stopper, and the reaction is continued at about 0° C. for 20 minutes, while stirring at a low speed to prevent the gel from going to pieces. After the reaction, the gel is transferred on a glass filter and then washed successively with acetone, a mixture of acetone and 5 mM HCl (1 : 1), and 5 mM HCl. The gel is further washed with 30 ml of dry acetone, after which the filter is covered with a polyvinyl chloride bag containing dry nitrogen gas and being attached to the top opening thereof, and suction is applied thereto for approximately 1 hour in order to dry the gel completely.

(2) Immobilization of the probes on gel

DNA probes synthesized on the support are cleaved with a conc. ammonia water and allowed to stand at 55° C. for 10 hours, followed by deprotection. The probes are concentrated under reduced pressure to dryness, and dissolved in 200 μl of 10 mM triethylamine acetate (TEAA) buffer. After elimination of protecting groups by ether extraction, the probes are concentrated once again to dryness, and dissolved in 180 μl of a coupling buffer (0.2M NaHCO$_3$ and 0.5M NaCl, pH 7.5). Then, 100 mg of the activated gel prepared in Step (1) is taken in a 1.5 ml Ependolf tube and mixed with the aforementioned DNA probes. The mixture is maintained at 25° C. for 24 hours with gentle agitation, resulting in an immobilization of the probe on the gel. After the reaction, the gel is removed from the supernatant by centrifugation at 2,000 rpm for 5 minutes to thereby obtain the immobilized probes.

5) Hybridization of the desired DNA fragment with the immobilized probe a) The DNA fragments mixture containing the desired DNA fragment linked to the linkers, which was obtained in Step 3), is dissolved in 100 μl of 2.4M tetraethylammonium chloride.

b) The resultant solution is subjected to denaturation treatment at 70° C. for 1 minute.

c) The immobilized probe 1 (5 mg) is added to this solution, and the mixture is allowed to stand at 20° C. for 10 minutes.

d) The immobilized probe 1 thus hybridized is precipitated by centrifugation (at 2,000 rpm for 15 seconds), and the supernatant is taken in another Eppendorf tube.

e) The immobilized probe is washed by addition of 50 μl of 2.4M tetraethylammonium chloride, and the hybridized probe is recovered once again by centrifugation at 2,000 rpm for 15 seconds. The supernatant is added to the Eppendorf tube in Step d).

f) To the hybridized probe separated in Step e), 2.4M tetraethylammonium chloride (100 μl) is added and the resultant suspension is subjected to denaturation treatment by heating at 70° C. for 10 minutes, followed by centrifugation at 2,000 rpm for 15 seconds to separate the hybridized DNA fragment from the immobilized probe. The supernatant containing the DNA fragment is recovered.

g) To the supernatant recovered in Step f), the immobilized probe 3 (5 mg) is added, and the mixture is allowed to stand at 20° C. for 10 minutes.

h) The mixture is centrifuged at 2,000 rpm for 15 seconds, and the supernatant is removed.

i) To the immobilized probe separated in Step h), 2.4M tetraethylammonium chloride (100 μl) is added, and the resultant suspension is subjected to centrifugation at 2,000 rpm for 15 seconds to recover the immobilized probe.

j) To the immobilized probe recovered in Step i), 2.4M tetraethylammonium chloride (100 μl) is added, and the resultant suspension is subjected to denaturation treatment by heating at 70° C. for 10 minutes, followed by centrifugation at 2,000 rpm for 15 seconds to separate the supernatant containing the DNA fragment from the immobilized probe. The supernatant is recovered and used for subsequent analysis (Sample 1).

k) The supernatant in Step e) is subjected to denaturation treatment at 70° C. for 1 minute, and the immobilized probe 2 (5 mg) is added thereto. The mixture is allowed to stand at 20° C. for 10 minutes.

l) The mixture is centrifuged at 2,000 rpm for 15 seconds, and the supernatant is removed.

m) The immobilized probe as the precipitate is added with 100 μl of 2.4M tetraethylammonium chloride, and the mixture is centrifuged again at 2,000 rpm for 15 seconds. The supernatant is removed.

n) To the hybridized probe thus recovered, 2.4M tetraethylammonium chloride (100 μl) is added, and the resultant suspension is subjected to denaturation treatment by heating at 70° C. for 10 minutes, followed by centrifugation at 2,000 rpm for 15 seconds to recover the supernatant.

o) To the supernatant recovered in Step n), the immobilized probe 4 (5 mg) is added, and the mixture is allowed to stand at 20° C. for 10 minutes.

p) The hybridized probe is recovered by centrifugation at 2,000 rpm for 15 seconds and washed wit 100 μl of 2.4M tetraethylammonium chloride. The probe is recovered by centrifugation at 2,000 rpm for 15 seconds. The probe thus recovered is suspended in 100 μl of 2.4M tetraethylammonium chloride, and the resultant suspension is subjected to denaturation treatment by heating at 70° C. for 10 minutes, followed by centrifugation at 2,000 rpm for 15 seconds to recover the supernatant. The supernatant thus recovered is used for subsequent analysis (Sample 2).

6) Identification of the DNA fragment recovered, and determination of its purity Samples 1 and 2 obtained in Step 5) are mixed each other, heated at 70° C. for 10 minutes, and then allowed to stand at 20° C. for 30 minutes (Sample 3).

Sample 3 (2 μl) was subjected to 2% agarose gel electrophoresis, and a single band was observed at the position of about 790 to 800 bp by autoradiography.

On the other hand, Sample 3 was also examined on the amount of desired DNA fragment recovered. Thus, on the basis of the amount of the starting pBR322 (1.0 μg; See Reaction mixture 1), theoritical amount of Eco RI - Pst I fragment is calculated as 173 ng. On the other hand, the amount of the desired DNA fragment recovered was 145 ng. On the basis of these data, the following equation gave 80% recovery of the desired DNA fragment.

$$\text{Recovery of desired DNA fragment} = \frac{145 \times \left(\frac{752}{795}\right)^*}{173} \times 100 = 80\%$$

*Note:
"752 stands for the number of nucleotides contained in the Eco RI - Pst I fragment, whereas "795" stands for the number of nucleotides contained in the Eco RI- Pst I fragment accompanied by the linker.

These results indicate that Fragment A of interest was successfully recovered in spite of the fact that the restriction enzymes used in the above Step 1), Sal I, Pvu II and Bal I, yielded other fragments of similar size to the desired Fragment A.

What is claimed is:

1. A method of extracting a particular nucleic acid fragment containing a nucleic acid sequence of interest from a nucleic acid or nucleic acids mixture, comprising the steps of:
   (1) digesting the nucleic acid or nucleic acids mixture with restriction enzymes to obtain a mixture of nucleic acid fragments, said restriction enzymes consisting of (A) two different enzymes capable of producing the particular nucleic acid fragment bearing predetermined and distinct restriction ends on its 5' and 3' terminals and (B) one or more restriction enzymes different from (A), for which the particular nucleic acid fragment contains no relevant restriction sites;
   (2) preparing two distinct DNA linkers capable of binding to the respective restriction ends of the particular nucleic acid fragment;
   (3) contacting the linkers and nucleic acid fragments under conditions sufficient to ligate complementary ends of the linkers and nucleic acid fragments;
   (4) subjecting the resulting reaction mixture to a first hybridization with an immobilized probe complementary to one of the linkers;
   (5) isolating the hybridized nucleic acid fragment from the probe;
   (6) subjecting the isolated nucleic acid fragment to a second hybridization with an immobilized probe complementary to the other linker; and
   (7) isolating the hybridized nucleic acid fragment from the probe.

2. The method of claim 1 wherein the nucleic acid is DNA.

3. The method of claim wherein the immobilized probe is a nucleic acid immobilized on an insoluble carrier.

4. The method of claim 3 wherein the nucleic acid is immobilized at its terminal.

5. The method of claim 3 wherein the nucleic acid is DNA.

6. The method of claim 3 wherein the insoluble carrier is naturally-occurring or synthetic organic or inorganic polymer membrane.

7. The method of claim 3 wherein the insoluble carrier is naturally-occurring or synthetic organic or inorganic polymer particle.

8. The method of claim 7 wherein the size of the particle is 0.1 $\mu$m–500 $\mu$m.

9. The method of claim 8 wherein the size is 1 $\mu$m–100 $\mu$m.

10. The method of claim 7 wherein the insoluble carrier is silica gel.

11. The method of claim 7 wherein the insoluble carrier is polystyrene.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 19 base pairs
( B ) TYPE: nucleic acid
( C ) STRANDEDNESS: both
( D ) TOPOLOGY: linear ( i i ) MOLECULE TYPE: cDNA ( x i ) SEQUENCE DESCRIPTION: SEQ ID NO:1:

GCAACCATGC CTAAGTTTG                    1 9

( 2 ) INFORMATION FOR SEQ ID NO:2:

( i ) SEQUENCE CHARACTERISTICS:
( A ) LENGTH: 23 base pairs
( B ) TYPE: nucleic acid
( C ) STRANDEDNESS: both
( D ) TOPOLOGY: linear ( i i ) MOLECULE TYPE: cDNA ( x i ) SEQUENCE DESCRIPTION: SEQ ID NO:2:

AATTCAAACT TAGGCATGGT TGC                2 3

( 2 ) INFORMATION FOR SEQ ID NO:3:

( i ) SEQUENCE CHARACTERISTICS:
( A ) LENGTH: 24 base pairs
( B ) TYPE: nucleic acid
( C ) STRANDEDNESS: both
( D ) TOPOLOGY: linear ( i i ) MOLECULE TYPE: cDNA ( x i ) SEQUENCE DESCRIPTION: SEQ ID NO:3:

TTCCGTATGG CATGCCTCCC TGCA               2 4

( 2 ) INFORMATION FOR SEQ ID NO:4:

( i ) SEQUENCE CHARACTERISTICS:
( A ) LENGTH: 20 base pairs
( B ) TYPE: nucleic acid
( C ) STRANDEDNESS: both
( D ) TOPOLOGY: linear (i i) MOLECULE TYPE: cDNA (x i) SEQUENCE DESCRIPTION: SEQ ID NO:4:

GGGAGGCATG CCATACGGAA 20